(12) United States Patent
Takagi et al.

(10) Patent No.: US 8,435,227 B2
(45) Date of Patent: May 7, 2013

(54) CATHETER FOR LEFT CORONARY ARTERY AND ENGAGING METHOD THEREFOR

(75) Inventors: Ayumu Takagi, Shizuoka (JP); Hiroyoshi Ise, Shizuoka (JP); Daisuke Nakashima, Shizuoka (JP); Tetsuya Fukuoka, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 389 days.

(21) Appl. No.: 12/892,313

(22) Filed: Sep. 28, 2010

(65) Prior Publication Data

US 2011/0077530 A1    Mar. 31, 2011

(30) Foreign Application Priority Data

Sep. 28, 2009  (JP) ................................. 2009-222976
Jul. 22, 2010  (JP) ................................. 2010-164879

(51) Int. Cl.
*A61M 25/00* (2006.01)

(52) U.S. Cl.
USPC ........................................................ 604/523

(58) Field of Classification Search ................. 604/523, 604/524–536, 96.01, 164.01, 95.01–95.05
See application file for complete search history.

(56) References Cited

U.S. PATENT DOCUMENTS 5,876,385 A * 3/1999 Ikari et al. .................... 604/523

FOREIGN PATENT DOCUMENTS

JP    3563540 B2    9/2004

* cited by examiner

*Primary Examiner* — Kevin C Sirmons
*Assistant Examiner* — Phillip Gray
(74) *Attorney, Agent, or Firm* — Kenealy Vaidya LLP (57) ABSTRACT

Disclosed herein is a catheter for a left coronary artery having a distal end for being introduced into an opening of the left coronary artery from an artery of an arm. The catheter can include a catheter main body including a main body portion of a substantially linear shape in a natural state thereof and a curved portion extending from the main body portion to form a portion that extends to the distal end and has a curved shape in a natural state thereof.

20 Claims, 8 Drawing Sheets

CATHETER FOR LEFT CORONARY ARTERY AND ENGAGING METHOD THEREFOR

This application claims the priority benefit under 35 U.S.C. §119 of Japanese Patent Application No. 2009-222976 filed on Sep. 28, 2009 and 2010-164879 filed on Jul. 22, 2010, which are hereby incorporated in their entireties by reference.

BACKGROUND

1. Field

The disclosed subject matter relates to a catheter for a coronary artery for treating and imaging the heart or a peripheral tissue of the heart and an engaging method for the catheter.

2. Description of the Related Art

Conventionally, catheters for imaging a coronary artery, catheters of the Judkins type, the Amplatz type and so forth. Usually, these types of catheters are introduced from a femoral artery by the Seldinger method or a sheathing method to selectively image a coronary artery.

Also, many different treatments for a peripheral region of the heart using a catheter are available at present. For example, percutaneous transluminal coronary angioplasty (PTCA) of ischemic heart disease treatment using a catheter with a balloon is available. With regard to this treatment, in order to insert a treatment catheter into a target blood vessel safely and efficiently, the performance of the treatment catheter is important, and a guiding catheter which softens a reaction caused by the insertion and provides sufficient backup force to assist smooth introduction is often required. Shapes of such a guiding catheter can be similar to those of the Judkins type, the Amplatz type and so forth which are similarly available as in the case of the imaging catheter for a coronary artery described above. Usually, a catheter having any of the above noted shapes is introduced from a femoral artery by the Seldinger method or the sheathing method to selectively assure introduction into a coronary artery, and then a treatment catheter such as a balloon catheter for PTCA is introduced into the inner face of the guiding catheter.

In the imaging or treatment processes for such conventional catheters, since the introduction site is a femoral region, in order to stanch a penetration site after the surgery, complete bed rest may be required. Accordingly, urination, defecation, and eating and drinking may be required to be carried out in a supine position, and there is a problem in that discomfort, such as discomfort associated with lumbago may be experienced by the patient. Further, where a catheter is introduced from a femoral region, there is the possibility that, even if the patient is in complete bed rest, bleeding may occur, and there is a problem in that such bleeding may reach the retroperitoneum and cause further complications. Also urination may be difficult when a patient is in a supine position, and in this instance, there is a problem that, through use of a urethral catheter, there is the possibility that a urinary tract infection may occur.

As a method for eliminating or preventing the problems described above, introduction of the catheter from an artery of an arm, particularly from a brachial artery or a radial artery, is considered effective. In particular, even when keeping a state in which a brachial penetrated site is stretched, the patent can walk immediately after the surgery, and urination, defecation, and eating and drinking can be carried out in an ordinary manner without lumbago and so forth. Further, the possibility of bleeding from the retroperitoneum and/or the contraction of a urinary tract infection can be prevented.

Figure 8:
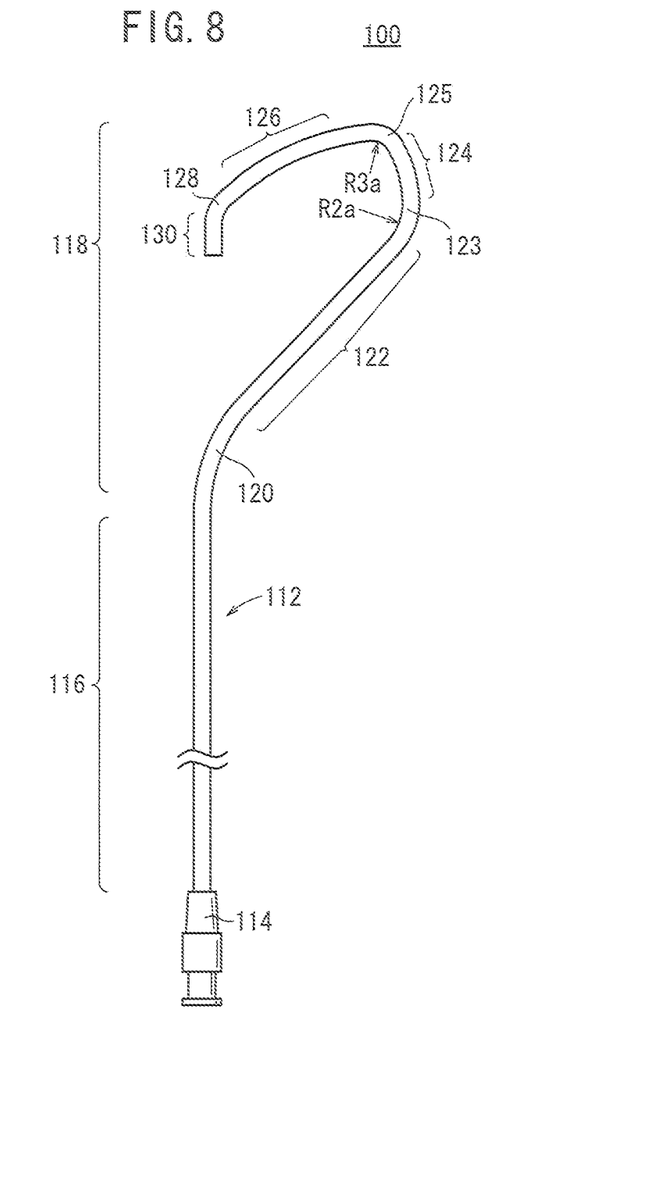
FIG. 8 is a partial plan view showing a catheter for the left coronary artery according to an exemplary comparative embodiment.

In view of such circumstances as described above, Japanese Patent No. 3,563,540 (hereinafter referred to as Patent Document 1) discloses a catheter for the left coronary artery having a shape suitable for introduction from an arm. FIG. 8 shows the catheter for the left coronary artery disclosed in Patent Document 1. Referring to FIG. 8, the catheter 100 for the left coronary artery includes a catheter main body 112 and a hub 114. The catheter main body 112 is configured from a substantially linear main body portion 116 and a distal end portion 118 having a curved shape. The distal end portion 118 is configured from a first substantially linear portion 122 continuing from the main body portion 116 through a first curved portion 120, a second substantially linear portion 124 continuing from the first substantially linear portion 122 through a second curved portion 123 curved in the opposite direction to that of the first curved portion 120, a third substantially linear portion 126 continuing from the second linear portion 124 through a third curved portion 125 curved in the same direction as that of the second curved portion 123, and a substantially linear extreme distal end portion 130 continuing from the third substantially linear portion 126 through a fourth curved portion 128 curved in the same direction as that of the third curved portion 125. The catheter 100 for the left coronary artery is shaped such that, when the distal end of the catheter 100 is positioned in the opening of the left coronary artery, the first curved portion 120 is introduced from the brachiocephalic artery into the aortic arch. The catheter 100 for the left coronary artery is shaped such that the second substantially linear portion 124 can contact with a wall of the aortic arch on an opposite side with respect to the opening of the left coronary artery.

Since the catheter 100 for the left coronary artery has a configuration as described above, it can be introduced from the artery of an arm, for example, from the brachial artery or the radial artery into the opening of the coronary artery without passing the femoral artery. As a result, the catheter can be introduced easily, reliably and quickly and the burden after surgery on the patient can be reduced.

SUMMARY

In procedures involving a coronary catheter it is sometimes helpful to be able to change the direction of the distal end of the catheter into or from a state in which the catheter distal end engages with the opening of the left coronary artery. In view of this type of operation, enhancement of the operability of the catheter would allow the doctor to carry out manual operation easily, reliably and quickly and contributes also to reduction of the burden on a patient.

Accordingly, it is desirable to further enhance the operability with respect to a catheter having a shape suitable for introduction from an arm.

For example, a catheter for the left coronary artery can be configured for introduction from an artery of an arm, for example, for the brachial artery or the radial artery The operability of the catheter can be enhanced, and an engaging method for the catheter for the left coronary artery can also be provided.

According to an aspect of the disclosed subject matter, there is provided a catheter for a left coronary artery having a distal end for being introduced into an opening of the left coronary artery from an artery of an arm (for example, from an artery of the right arm), including a catheter main body including a main body portion of a substantially linear shape in a natural state thereof and a curved portion extending from the main body portion to form a portion to the distal end and having a curved shape in a natural state thereof, the curved portion including an inclined portion extending in an inclined direction with respect to the main body portion through a first curved portion from the main body portion, a substantially linear portion continuing from the inclined portion through a second curved portion curved in the opposite direction to that of the first curved portion, and an extreme distal end portion of a substantially linear shape continuing from the substantially linear portion through a third curved portion curved in the same direction as that of the second curved portion, the catheter for a left coronary artery being shaped such that the first curved portion is positioned in a brachiocephalic artery when the extreme distal end portion is positioned in the opening of the left coronary artery and such that the second curved portion can contact with an inner wall of an aorta ascendens on the opposite side to the opening of the left coronary artery.

In the above described exemplary catheter for a left coronary artery, when the extreme distal end portion is positioned at an opening of the left coronary artery, the second curved portion is contacted with a wall of the aorta on the opposite side to the opening of the left coronary artery and the second curved portion thus placed into a curved state carries out backup support. When the portion of the catheter for a left coronary artery which contacts with the wall of the aorta is curved in this manner, the contact length with the wall of the aorta decreases from that where the portion which contacts with the wall of the aorta has a linear shape. Therefore, even where the catheter for a left coronary artery carries out backup support, it is easy to change the direction of the curved portion around a fulcrum provided by the second curved portion. Accordingly, it is easy to change the direction of the extreme distal end portion positioned at the opening of the left coronary artery.

Further, in the catheter for a left coronary artery of the present embodiment wherein the portion which contacts with a wall of the aorta is curved, since the contact area with the wall of the aorta is smaller than that where the portion which contacts with the wall of the aorta has a linear shape, it is possible to raise the contact pressure between the second curved portion and the wall of the aorta. Consequently, when it is tried to change the direction of the extreme distal end portion positioned at the opening of the left coronary artery, the position of the second curved portion at which the backup support is carried out is less likely to be displaced. Accordingly, the extreme distal end portion is less likely to be disengaged from the opening of the left coronary artery.

In the exemplary catheter for a left coronary artery described above, the portion between the inclined portion and the substantially linear portion thereof can be configured only from the second curved portion. However, in the conventional catheter for a left coronary artery described hereinabove with reference to FIG. 8, the portion between the first substantially linear portion and the third substantially linear portion is configured from two curved portions and one substantially linear portion. This difference, where the relative positional relationship between the inclined portion and the substantially linear portion of the catheter for a left coronary artery of the disclosed subject matter, that is, the distance between and the angle defined by the two substantially linear portions, and the relative positional relationship between the first substantially linear portion and the third substantially linear portion of the conventional catheter for a left coronary artery are same, with the catheter for a left coronary artery of the disclosed subject matter, it is possible to set the radius of curvature of the second curved portion greater than those of the second curved portion and the third curved portion of the conventional catheter for a left coronary artery. Generally in a catheter, as the radius of curvature of a curved portion decreases, a kink or torsion is more liable to occur when torque is applied. However, with the catheter for a left coronary artery of the disclosed subject matter, since the radius of curvature of the second curved portion is set to a comparatively great dimension, the resisting property to occurrence of a kink or torsion is raised. Therefore, torque can be applied readily from the proximal end side to the catheter distal end, that is, to the extreme distal end portion, and the direction of the catheter distal end can be changed readily. Further, when the direction of the extreme distal end portion is to be changed, since the displacement of the substantially linear portion caused by the change of the direction of the extreme distal end portion is absorbed by elastic deformation of the second curved portion to maintain the backup force, the extreme distal end portion is less likely to be disengaged from the opening of the left coronary artery.

In this manner, the catheter for a left coronary artery of the disclosed subject matter is further improved in operability.

The substantially linear portion can extend in a warped direction and at an angle with respect to the inclined portion and can be separated from each other by the second curved portion.

With the catheter for a left coronary artery, insertion of the catheter distal end into the opening of the left coronary artery from an artery of an arm is further facilitated.

The curved portion can be shaped such that, when the extreme distal end portion is positioned in the opening (ostium) of the left coronary artery, the extreme distal end portion is inclined with respect to an axial direction of the opening of the left coronary artery.

With the catheter for a left coronary artery, it is possible to prevent the extreme distal end portion from excessively advancing into the coronary artery such that the extreme distal end portion can engage at an appropriate position with the opening of the left coronary artery.

The curved portion can be configured to exist in one, single plane.

With the catheter for a left coronary artery, since the aortic arch, aorta ascendens and opening of the left coronary artery exist on a substantially same plane, where the curved portion is configured in such a manner as described above, insertion of the extreme distal end portion from the artery of the arm into the opening (ostium) of the left coronary artery is further facilitated.

The inclined portion can be curved in the same direction as that of the first curved portion.

With the catheter for a left coronary artery, if the extreme distal end portion which is the catheter distal end is engaged with the opening of the left coronary artery and the second curved portion is in contact with the inner wall of the aorta to establish a backup support state, then the second curved portion can be pressed against the inner wall of the aorta by force of the inclined portion which tends to restore the catheter its original curved shape. Therefore, the stability of the backup support is increased and the operability is further improved.

According to another aspect of the disclosed subject matter, there is provided a catheter for a left coronary artery having a distal end configured to be engaged with an opening (ostium) of the left coronary artery, the catheter for the left coronary artery being configured such that the distal end thereof is introduced into the opening of the left coronary artery from an artery of an arm. The catheter for a left coronary artery can include a catheter main body including a main body portion having a substantially linear shape in a natural state thereof and a curved portion extending from the main body portion to form a portion to the distal end and having a curved shape in a natural state thereof, the curved portion including an inclined portion extending from the main body portion in an inclined direction with respect to the main body portion through a first curved portion, a substantially linear portion continuing from the inclined portion through a second curved portion curved in the opposite direction to that of the first curved portion, and an extreme distal end portion having a substantially linear shape continuing from the substantially linear portion through a third curved portion curved in the same direction as that of the second curved portion. The catheter for a left coronary artery can be shaped such that the first curved portion is positioned in a brachiocephalic artery when the extreme distal end portion is positioned in the opening (ostium) of the left coronary artery and such that the second curved portion can contact with an inner wall of an aorta ascendens on the opposite side to the opening of the left coronary artery. The catheter for the left coronary artery can also be configured such that the second bent portion is positioned on a wall of the aorta, the extreme distal end portion is moved to the neighborhood of the opening of the left coronary artery, the curved portion is rotated around a center of rotation provided by the second curved portion positioned on the wall of the aorta, and such that the extreme distal end portion is engaged with the opening of the left coronary artery.

According to a further aspect of the disclosed subject matter, there is provided an engagement method for engaging a distal end of a catheter for a left coronary artery with an opening (ostium) of the left coronary artery, the catheter for the left coronary artery can be configured such that the distal end thereof is introduced into the opening of the left coronary artery from an artery of an arm. The catheter for a left coronary artery can include a catheter main body including a main body portion having a substantially linear shape in a natural state thereof and a curved portion extending from the main body portion to form a portion extending to the distal end and having a curved shape in a natural state thereof, the curved portion including an inclined portion extending from the main body portion in an inclined direction with respect to the main body portion through a first curved portion, a substantially linear portion continuing from the inclined portion through a second curved portion curved in the opposite direction to that of the first curved portion, and an extreme distal end portion of a substantially linear shape continuing from the substantially linear portion through a third curved portion curved in the same direction as that of the second curved portion. The catheter for a left coronary artery can be shaped such that the first curved portion is positioned in a brachiocephalic artery when the extreme distal end portion is positioned in the opening of the left coronary artery and such that the second curved portion can contact with an inner wall of an aorta ascendens on the opposite side to the opening of the left coronary artery. The engaging method can include positioning the second bent portion on a wall of the aorta, moving the extreme distal end portion to the neighborhood of the opening of the left coronary artery, rotating the curved portion around the center of rotation provided by the second curved portion positioned on the wall of the aorta, and engaging the extreme distal end portion with the opening of the left coronary artery. These processes can be executed consecutively, non-consecutively, or spaced with other procedures/processes therebetween.

With the above described catheter for a left coronary artery and engaging method for the catheter for a left coronary artery, since the second curved portion of the curved portion can contact with a wall of the aorta in a manner that does not invoke a line-contact but instead in a manner in which contact can be approximate to point contact, the position of the extreme distal end portion can be readily adjusted by rotating the second curved portion. Consequently, the engagement of the extreme distal end portion with the opening of the left coronary artery can be carried out readily and rapidly.

In summary, with the above described catheters for a left coronary artery of the, when the catheter distal end is introduced into an opening of the left coronary artery, the second curved portion can be contacted with an inner wall of the aorta. Therefore, it is easy to change the direction of the curved portion around a fulcrum provided by the second curved portion, and accordingly, the direction of the catheter distal end can be changed readily. Besides, since the contact pressure between the second curved portion and the inner wall of the aorta can be raised to improve the stability of backup support, the extreme distal end portion is less likely to be disengaged from the opening of the left coronary artery. Therefore, the catheters for a left coronary artery provide further improved operability.

With the above described engaging method for a catheter for a left coronary artery, engagement of the extreme distal end portion with an opening of the left coronary artery can be carried out readily and rapidly.

DETAILED DESCRIPTION OF EXEMPLARY EMBODIMENTS

In the following, catheters for the left coronary artery and engaging methods for the catheter for the left coronary artery according to exemplary embodiments of the disclosed subject matter are described with reference to the drawings.

Figure 1:
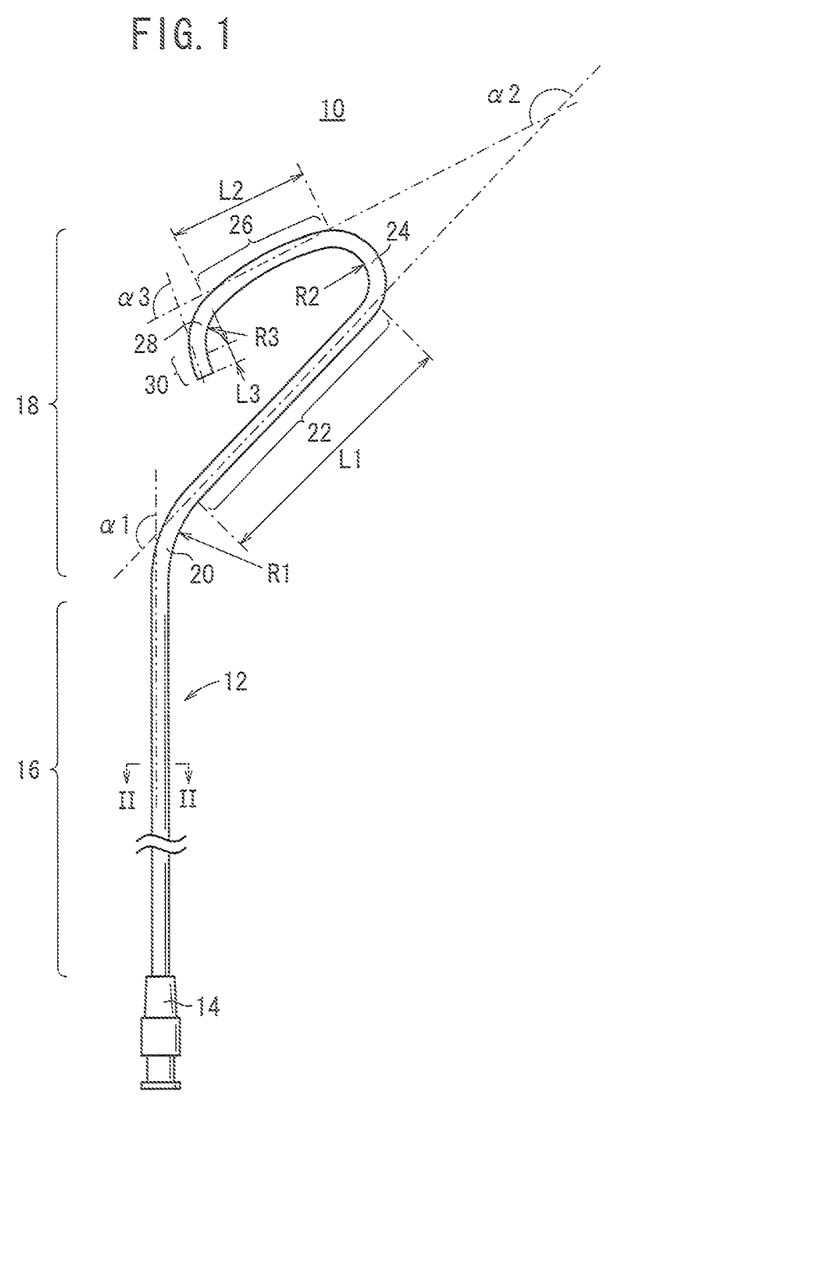
FIG. 1 is a partial plan view showing an example of a catheter for the left coronary artery according to an embodiment of the disclosed subject matter.

FIG. 1 shows a catheter for the left coronary artery 10 (hereinafter referred to sometimes as catheter 10) according to an exemplary embodiment of the disclosed subject matter. The catheter 10 can be configured such that the distal end thereof can be introduced into the opening (ostium) of the left coronary artery from an artery of an arm, for example, from an artery of the right arm.

In particular, referring to FIG. 1, the catheter 10 can include a catheter main body 12 including a hollow structure having flexibility, and a hub 14 formed at the proximal end of the catheter main body 12. The hub 14 can be configured to function as an injection port for injecting contrast medium or the like.

In order to allow the catheter 10 to be introduced from a brachial artery of a human being, for example from a radial artery, the outer diameter of the catheter main body 12 can be set to 2.7 mm or less, and possibly less than 2.1 mm, over the overall length thereof.

The catheter main body 12 can include a main body portion 16 having a substantially linear shape in a natural state, and a curved portion 18 extending from the main body portion 16 to form a portion extending to the distal end and having a curved shape in a natural state. Here, the "natural state" signifies a state in which no external force is applied, and the term is used in the following description so as to have similar meaning.

The main body portion 16 can have a substantially linear shape in a natural state. Although the length of the main body portion 16 is not particularly limited, it can be 400 to 1,000 mm for certain applications.

The curved portion 18 can be configured from an inclined portion 22 extending in an inclined direction with respect to the main body portion 16 from the main body portion 16 via a first curved portion 20, a substantially linear portion 26 continuing from the inclined portion 22 via a second curved portion 24 curved in the opposite direction to that of the first curved portion 20, and a substantially linear extreme distal end portion 30 continuing from the substantially linear portion 26 via a third curved portion 28 curved in the same direction as that of the second curved portion 24. Further, the curved portion 18 can be shaped such that the components from the first curved portion 20 to the extreme distal end portion 30 exist in one single plane.

The first curved portion 20 can have a curved shape, as shown in FIG. 1, which can be a shape that is curved in a clockwise direction from the main body portion 16, in a natural state. In the present embodiment, the first curved portion 20 is set such that the angle α1 formed by the main body portion 16 and the inclined portion 22 ranges from 90 to 150°, and possibly from 100 to 140°. If the angle α1 exceeds 150°, then there is the possibility that the catheter 10 may excessively stretch a joining portion of the subclavian artery and the brachiocephalic artery and give discomfort to the patient. On the other hand, where the angle α1 is less than 90°, it may be difficult to insert the extreme distal end portion 30, which is the catheter distal end, into the opening of the left coronary artery, and, even if the extreme distal end portion 30 is inserted into the opening of the left coronary artery, it may be difficult to obtain sufficient backup force.

Where the angle α1 is set within the range described above, sufficient repulsive force is generated when a guide wire is pulled out from the catheter 10 inserted from the brachiocephalic artery into the aorta ascendens and restores an original shape thereof. Consequently, the catheter distal end can be directed to and introduced into the opening of the left coronary artery easily, reliably and quickly only utilizing the repulsive force without the necessity for certain operations such as application of torque or the like. Further, while the radius (curve radius) R1 curvature of the first curved portion 20 is not particularly limited, it is possible in certain applications to set the radius R1 of curvature to approximately 30 to 100 mm in a natural state.

The inclined portion 22 can have a substantially linear shape in a natural state. While the length L1 of the inclined portion 22 is not particularly limited, it is possible in certain applications to set the length L1 to approximately 30 to 80 mm.

The second curved portion 24 has a shape curved in a direction opposite to that of the first curved portion 20 which, as shown in FIG. 1, is a shape curved in the counterclockwise direction from the inclined portion 22, in a natural state. While the radius (curve radius) R2 or curvature of the second curved portion 24 is not particularly limited, it is possible in certain applications to set the radius R2 of curvature to approximately 5 to 20 mm in a natural state. Further, while the angle α2 formed by the inclined portion 22 and the substantially linear portion 26 with the second curved portion 24 interposed therebetween is not particularly limited, it is possible in certain applications to set the angle α2 to approximately 120 to 175° in a natural state, and sometimes to approximately 140 to 170°.

The shape of the second curved portion 24 can be set such that it usually contacts with an inner wall of the aorta, particularly with the right wall of the aorta ascendens, on the opposite side to the opening of the left coronary artery upon self-retention. Consequently, the catheter distal end may be engaged with the opening of the left coronary artery to allow for sufficient backup force to be applied, and, in a guide catheter used together with a catheter for treatment, operation of a catheter for treatment to be inserted into the lumen of the guide catheter can be assisted with certainty.

The substantially linear portion 26 has a substantially linear shape in a natural state and extends in a warped direction with respect to the inclined portion 22 as positioned by the second curved portion 24. In other words, the substantially linear portion 26 can have a slight bend along its length as compared to the inclined portion such that the bend is concave in a direction facing towards the inclined portion. The length L2 of the substantially linear portion 26 can be set so as to substantially coincide with the distance from the aorta ascendens on the substantially opposite side to the opening of the left coronary artery upon self-retention to the opening of the left coronary artery. Consequently, the second curved portion 24 can contact with certainty with the right wall of the aorta ascendens so that disengagement of the catheter distal end from the opening of the left coronary artery can be prevented. In particular, the length L2 can be set to approximately 10 to 100 mm, and in certain applications, the length L2 can be set to approximately 20 to 50 mm.

The third curved portion 28 has a curved shape in the same direction as that of the second curved portion 24 which, as shown in FIG. 1, can be a curved shape in the counterclockwise direction after leaving the substantially linear portion 26, in a natural state. While the angle α3 formed by the substantially linear portion 26 and the extreme distal end portion 30 with the third curved portion 28 interposed therebetween is not particularly limited, it is possible for certain applications to set the angle α3 to approximately 30 to 150° in a natural state and in certain other applications to approximately 90 to 130°. Further, while the radius (curving radius) R3 of curvature of the third curved portion 28 is not particularly limited, it is possible to set the curvature radius R3 to approximately 5 to 20 mm in a state in which external force is not applied.

The extreme distal end portion 30 has a substantially linear shape in a natural state. The length L3 of the extreme distal end portion 30 can be set such that the extreme distal end portion 30 can be inserted into and self-retained at the opening of the left coronary artery with certainty without excessively entering into the opening of the left coronary artery, and can be particularly set to approximately 5 to 50 mm. The curved portion 18 can be shaped such that, when the extreme distal end portion 30 is positioned at the opening of the left coronary artery, the extreme distal end portion 30 is inclined with respect to the axial direction of the left coronary artery (i.e., with the longitudinal axis of the left coronary artery).

In the catheter 10 configured in such a manner as described above, the angles α1 to α3, curvature radiuses R1 to R3 and lengths L1 to L3 may be set, for example, in a manner as given to configuration examples 1 to 4 described below.

CONFIGURATION EXAMPLE 1

α1: 134°
α2: 162°
α3: 104°
R1: 43 mm
R2: 16 mm
R3: 11 mm
L1: 59 mm
L2: 25 mm
L3: 4 mm

CONFIGURATION EXAMPLE 2

α1: 145°
α2: 174°
α3: 110°
R1: 50 mm
R2: 20 m
R3: 15 mm
L1: 65 mm
L2: 35 mm
L3: 6 mm

CONFIGURATION EXAMPLE 3

α1: 108°
α2: 155°
α3: 92°
R1: 35 mm
R2: 11 mm
R3: 8 mm
L1: 40 mm
L2: 21 mm
L3: 3 mm

CONFIGURATION EXAMPLE 4

α1: 130°
α2: 160°
α3: 103°
R1: 42 mm
R2: 17 mm
R3: 12 mm
L1: 50 mm
L2: 45 mm
L3: 4 mm

Figure 2:
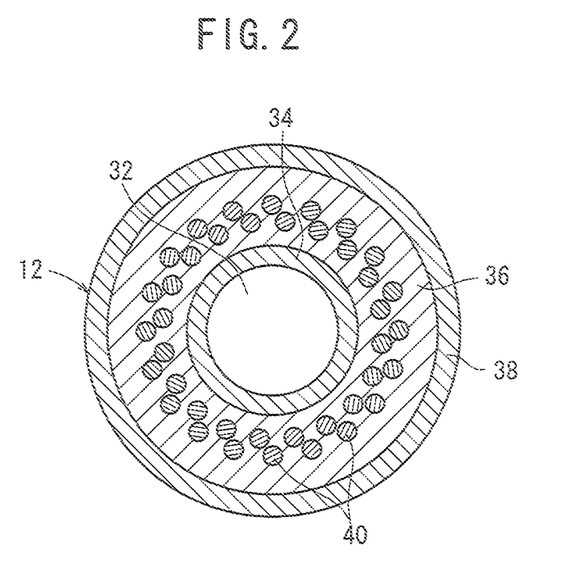
FIG. 2 is a sectional view of the catheter for the left coronary artery of FIG. 1 taken along line II-II.

FIG. 2 is a sectional view of the catheter 10 for the left coronary artery taken along line II-II of FIG. 1. Referring to FIG. 2, a lumen 32 is formed at a substantially central location of the catheter main body 12. The lumen 32 is open at the distal end of the catheter main body 12.

Further, the catheter main body 12 can be structured such that an inner layer 34, an intermediate layer 36 and an outer layer 38 are laminated concentrically from the inner side toward the outer side. Since the catheter main body 12 can be configured in this manner, there are advantages that a bend of the catheter main body 12 can be prevented and that the component materials, compounding ingredients, surface properties and so forth of the layers can be changed such that advantages associated with each of them can be shared.

As the component materials of the inner layer 34, intermediate layer 36 and outer layer 38, a polyamide-based resin such as nylon 11, nylon 12 or nylon 6, a polyester-based polyamide-based resin such as, for example, Grilax (trade name, by DIC corp.), a polyether-based polyamide resin such as, for example, Pebax (trade name, by Atochem), polyurethane, an ABS resin, a polyester elastomer resin, polyurethane elastomer resin, a fluorocarbon-based resin such as PFA, PTFE or ETFE, and other materials generally known in the art for use with catheters can be used. Particularly if an ABS resin or nylon is used as the component material(s) of the inner layer 34, intermediate layer 36 and outer layer 38, a suitable strength can be provided to the curved portion 18. Further, if a fluorocarbon-based resin, such as PTFE, is used for the inner layer 34, then the operability of a guide wire 48 (refer to FIG. 3) for being inserted into the lumen 32 or a catheter for treatment may be improved. It is to be noted that, since insertion of the catheter 10 may be carried out while the position thereof is being confirmed under X-ray radioscopy, a radiopaque material such as, for example, barium sulfate, bismuth oxide, tungsten, or other known radiopaque material can be used or compounded in a material from which the catheter main body 12 is formed.

Further, although the thickness of the inner layer 34, intermediate layer 36 and outer layer 38 is not particularly limited, in the example shown, the inner layer 34 has a thickness smaller than that of the intermediate layer 36 and the outer layer 38. Further, the inner layer 34, intermediate layer 36 and outer layer 38 can be adhered to each other by a suitable bonding agent or fusion bonded to each other by heat or else molded integrally by coating molding or the like. It is to be noted that the outer layer 38 and the intermediate layer 36 may be formed as a first layer (not shown) made of the same resin.

In the intermediate layer 36, a metal mesh 40 having a role as a reinforcing member can be embedded over an overall periphery thereof. The metal mesh 40 may be provided in a contacting relationship with the outer surface of the inner layer 34. The metal mesh 40 can be embedded, in the longitudinal direction of the catheter 10, over a substantially overall length of the catheter main body 12 except in a predetermined length from the distal end of the catheter main body 12. The position of the end of the metal mesh 40 can be within a range of 0.5 to 150 mm, for example from 1 to 100 mm, from the distal end of the catheter main body 12.

By embedding such a metal mesh 40 as just described, it is possible to prevent the catheter main body 12 from bending and to improve the torque transferability when the catheter main body 12 is rotated. The cross section of a wire which configures the metal mesh 40 may be a circular shape, a rectangular shape, a substantially elliptical shape, or other known shape.

It is to be noted that the reason why the metal mesh 40 is not necessarily embedded over the predetermined length from the distal end of the catheter main body 12 is that, if the metal mesh 40 extends to the extreme end of the catheter main body 12, then there is the possibility that the blood vessel wall may be damaged by the distal end of the catheter and, depending upon the material, if the metal mesh 40 extends to the neighborhood of the distal end of the catheter, then the catheter may become so hard that the distal end of the catheter becomes liable to enter the left ventricle without entering the opening of the coronary artery by manual operation hereinafter described. The distal end of the catheter 10 of the disclosed subject matter is not typically configured such that it is used in such a state that it reaches the left ventricle or the left atrium.

It is to be noted, however, that, if the metal mesh 40 does not exist at a portion of a length exceeding 150 mm from the distal end of the catheter main body 12, then the torque transferability mentioned hereinabove may not sometimes be obtained.

It is to be noted that the length of the portion at which the metal mesh 40 is not provided can be determined suitably depending upon the material, the difference between the inner and outer diameters, that is, the total thickness of the inner layer 34, intermediate layer 36 and outer layer 38, and so forth of the catheter main body 12. For example, as the difference between the inner and outer diameters of the catheter main body 12 increases, or as the elastic force of the material increases, the length of the portion over which the metal mesh 40 is not provided can be increased.

As a particular example of the metal mesh 40, a mesh formed from stainless steel, stainless steel spring wires, tungsten, Ni—Ti, wires of a small diameter such as carbon fibers, or other known meshes, may be used, and the line diameter can be, for example, approximately 0.01 to 0.2 mm.

The catheter 10 according to the embodiment of FIG. 1 can be basically configured in such a manner as described above, and operation and effects of the catheter 10 are described below. The following description is directed to an example of a method of use of the catheter 10 wherein the catheter 10 is used as a guiding catheter which is used together with a treatment catheter.

Figure 3:
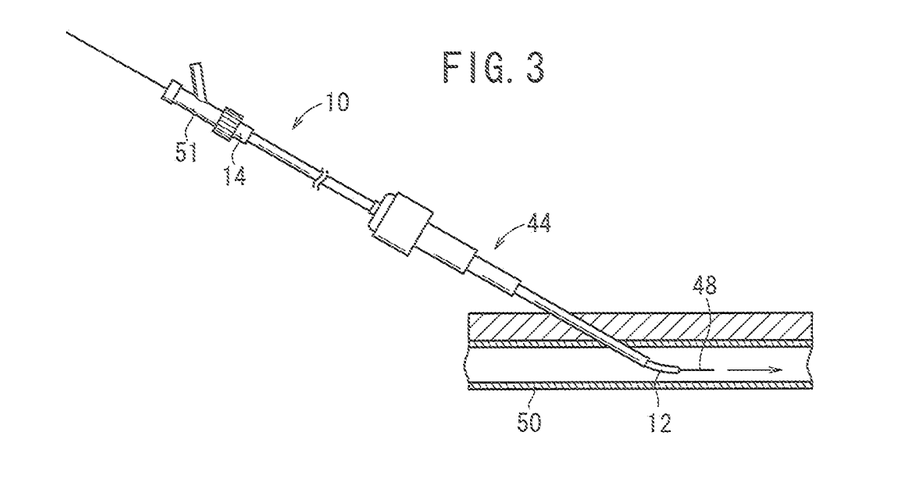
FIG. 3 is a schematic view illustrating a method for introducing the catheter for the left coronary artery of FIG. 1 into a blood vessel.

Referring to FIG. 3, a brachial artery or radial artery 50 can be punctured with a catheter introducer 44 by the Seldinger method, and the catheter 10 in a state in which the guide wire 48 is inserted is inserted into the catheter introducer 44. Then, in a state in which the guide wire 48 precedes to the distal end of the catheter main body 12, the distal end of the catheter main body 12 is inserted into the brachial artery or radial artery 50 from an opening at the distal end of the catheter introducer 44.

Figure 4:
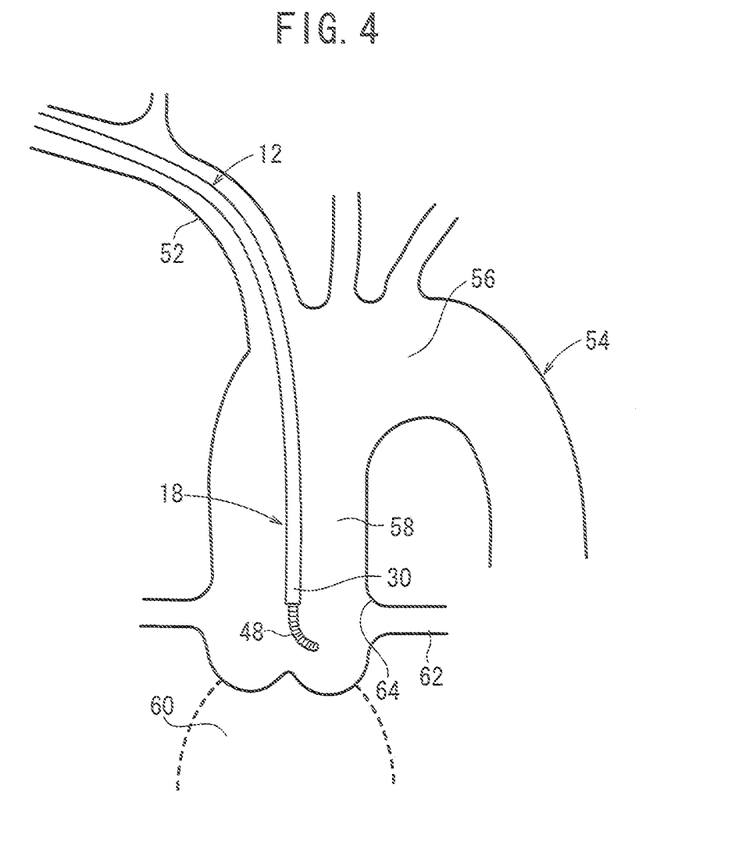
FIG. 4 is a schematic view showing an example of a method of use for the catheter for the left coronary artery of FIG. 1 and is a view showing the catheter for the left coronary artery of FIG. 1 in a state in which the distal end of the catheter for the left coronary artery is introduced to the proximity of the left coronary artery by a guide wire.

Then, the catheter 10 and the guide wire 48 are fed gradually in the direction indicated by an arrow mark in FIG. 3 so that they are inserted into the aorta ascendens 58 through the aortic arch 56 of the aorta 54 as shown in FIG. 4. Thereupon, operation of a suitable combination of insertion and removal of the guide wire 48 and back and forth movement and rotation of the catheter 10 can be carried out so that the distal end of the catheter main body 12 may pass through a bent portion of a blood vessel.

As shown in FIG. 4, the catheter 10 introduced into the aorta ascendens 58 from the brachiocephalic artery 52 is introduced to the neighborhood of the left ventricle 60. Since the curved portion 18 of the catheter main body 12 can be formed in conformity with a bend of the subclavian artery, the catheter 10 advances while rotating a little in a blood vessel until it reaches the aorta ascendens 58. As a result, when the curved portion 18 reaches the aorta ascendens 58, the extreme distal end portion 30 is likely to be automatically directed to the opening of the left coronary artery 62, that is, to the left coronary artery opening 64. If the catheter 10 is thereafter inserted as it is, then the second curved portion is brought into contact with the Valsalva sinus. It is to be noted that, at this time, since the curved portion 18 of the catheter main body 12 is in a state stretched by the guide wire 48 inserted in the lumen 32, it can exhibit a substantially linear shape.

Thereafter, if the guide wire 48 is pulled off from the catheter main body 12, then the curved portion 18 restores to its original curved shape. By repulsive force generated by such shape restoration, the catheter distal end is directed to the left coronary artery opening 64, and the second curved portion 24 of the curved portion 18 is brought into contact at an apex thereof with an aorta ascendens right wall 66 positioned on the opposite side to the left coronary artery opening 64. At this time, if the catheter distal end is inserted into the left coronary artery opening 64, then a state in which the catheter distal end, that is, the extreme distal end portion 30, engages with the left coronary artery opening 64 can be established. Further, at this time, since the second curved portion 24 of the curved portion is positioned along a curve extending from the aorta ascendens 58 to the subclavian artery, the catheter 10 can be fixed better.

Figure 5:
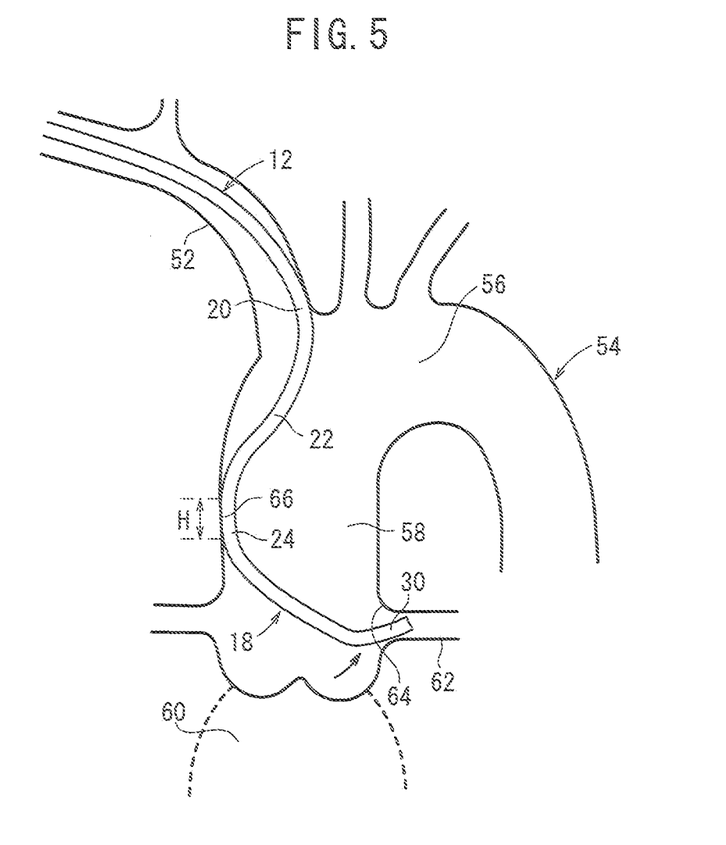
FIG. 5 is a similar view as FIG. 4 but showing the catheter for the left coronary artery of FIG. 1 in another state in which the distal end of the catheter for the left coronary artery is engaged with the opening of the left coronary artery.

Engagement of the catheter 10 with the left coronary artery opening 64 may be carried out by positioning the second curved portion 24 on a wall of the aorta, that is, on the aorta ascendens right wall 66, moving the extreme distal end portion 30 toward the left coronary artery opening 64, rotating the curved portion 18 around the center of rotation provided by the second curved portion 24 positioned on the aorta wall, and engaging the extreme distal end portion 30 with the left coronary artery opening 64.

In particular, when the curved portion 18 restores to its original curved state, if the catheter distal end is not inserted in the left coronary artery opening 64, then suitably slight rotation may be applied to the proximal end portion of the catheter 10 to rotate the extreme distal end portion 30 around the center of rotation provided by an apex of the second curved portion 24 to direct the extreme distal end portion 30 to the left coronary artery opening 64. Consequently, the catheter distal end can be readily inserted into the left coronary artery opening 64. Further, the proximal end portion of the catheter 10 can be further rotated in this state to rotate the extreme distal end portion 30 around the center of rotation provided by the apex of the second curved portion 24 to adjust the direction of the extreme distal end portion 30 in the left coronary artery opening 64. Since the second curved portion 24 can be configured to contact with the aorta wall in a manner that does not form a line-contact but instead forms a substantially point contact, the position of the extreme distal end portion 30 can be readily adjusted by rotating the second curved portion 24. Consequently, the engagement of the extreme distal end portion 30 with the left coronary artery opening 64 can be carried out readily and rapidly.

In the state in which the catheter distal end engages with the left coronary artery opening 64, the second curved portion 24 can contact with the aorta ascendens right wall 66 positioned on the opposite side to the left coronary artery opening 64 to carry out backup support at the second curved portion 24 in the curved state. Since the catheter main body 12 can be shaped in such a manner as described hereinabove, high backup force can be exerted. Since the curved portion 18 of the catheter main body 12 can be fixed well to the aorta ascendens 58 by the backup force, the catheter distal end is less likely to be disengaged from the left coronary artery opening 64. At this time, the first curved portion 20 contacts with the blood vessel wall in a range proximate to the aortic arch 56 in the brachiocephalic artery 52. By such contact, the first curved portion 20 retains the position of the curved portion 18 in the aorta 54.

Further, if the inclined portion 22 which exhibits a substantially linear shape in a natural state thereof is set to a length over which the catheter distal end is curved in a state in which it engages with the left coronary artery opening 64 as shown in FIG. 5, then the pressing of the second curved portion 24 upon the aorta ascendens right wall 66 is assisted by force of the inclined portion 22 which tends to restore its linear state, and consequently, the backup force increases. Consequently, further stabilized backup support is achieved.

As apparent from the foregoing description, the catheter 10 can be configured such that when in use, the second curved portion 24 is positioned on a wall of the aorta, the extreme distal end portion 30 is moved to the neighborhood of the left coronary artery opening 64, the curved portion 18 is rotated around the center of rotation provided by the second curved portion 24 positioned on the aorta wall, and the extreme distal end portion 30 is engaged with the left coronary artery opening 64.

Since the shape of the catheter 10 according to the present embodiment is defined as described above, it can be introduced into the left coronary artery opening 64 readily, safely and rapidly by the operation described above without the necessity for complicated operation or for high torque transferability.

After the catheter distal end is inserted into the left coronary artery opening 64 by the operation described above, the guide wire 48 can be pulled out from the lumen 32 and a connector can be connected to a Y connector 51 (refer to FIG. 3) mounted at a rear end of the hub 14 to inject contrast medium or other medical media or device(s). In this example, the injected contrast medium passes through the lumen 32 and is jetted from the end opening of the lumen 32 into the left coronary artery 62 which is a target region. Consequently, confirmation of the inserted position of the catheter distal end in the left coronary artery opening 64 and imaging of the left coronary artery 62 are permitted.

Then, a treatment catheter (not shown) such as a PTCA balloon catheter can be inserted through a rear end portion of the Y connector 51 and the lumen 32. Generally, in such treatment catheters, the catheter main body has rigidity, and when a treatment catheter is operated, it is frequently pushed back by a reactive action to the operation from the left coronary artery which is a target range for self-retention. If this action occurs, then it may be difficult to insert the treatment catheter into the target range. Accordingly, the backup force of the catheter 10 described above is significant.

Incidentally, in the comparative catheter 100 for the left coronary artery described hereinabove with reference to FIG. 8, since the second substantially linear portion 124 contacts with an aorta wall, that is, with the right wall of the aorta ascendens, the contact length between the catheter and aorta 100 is comparatively long. In contrast, in the catheter 10 according to the present embodiment, the second curved portion 24 contacts with the aorta ascendens right wall 66 as seen in FIG. 5, and the contact length H between the catheter 10 and aorta is short in comparison with that of the comparative catheter 100. Consequently, even if the catheter 10 carries out backup support, the direction of the curved portion 18 can be changed readily around a fulcrum provided by the second curved portion 24, and accordingly, the direction of the catheter distal end, that is, the extreme distal end portion 30, positioned in the left coronary artery opening 64 can be changed readily. Therefore, the catheter 10 can be provided with enhanced operability. The contact length H can be smaller than approximately 10 mm.

Further, in the catheter 10 of the present embodiment wherein a portion thereof for contacting with an inner wall of the aorta is curved, the contact area with the inner wall of the aorta can be smaller than that in the comparative catheter 100 of FIG. 8 wherein the region in which the catheter 100 contacts with an inner wall of the aorta, that is, the second substantially linear portion 124, has a linear shape. Therefore, the contact pressure between the second curved portion 24 and the inner wall of the aorta can be made higher. Consequently, when it is tried to change the direction of the catheter distal end, that is, of the extreme distal end portion 30, positioned in the left coronary artery opening 64, the position of the second curved portion 24 for which backup support is carried out is less likely to move. Accordingly, the catheter distal end is less likely to be disengaged from the left coronary artery opening 64.

While, in the catheter 10 of the present embodiment, the portion between the inclined portion 22 and the substantially linear portion 26 can be configured only from the second curved portion 24, in the comparative catheter 100 shown in FIG. 8, the portion between the first substantially linear portion 122 which corresponds to the inclined portion 22 and the third substantially linear portion 126 which corresponds to the substantially linear portion 26 is configured from the two curved portions 123 and 125 and the second substantially linear portion 124. The relative positional relationship between the inclined portion 22 and the substantially linear portion 26 of the catheter 10 of the present embodiment, that is, the distance between and the angle α2 defined by the two portions 22 and 26 and the relative positional relationship between the first portion 122 and the third substantially linear portion 126 of the comparative catheter 100 can be the same. In such a case, with the catheter 10 of the present embodiment, it is possible to set the radius R2 of curvature of the second curved portion 24 greater than the radii R2a and R3a of curvature of the second curved portion 123 and the third curved portion 125 of the conventional catheter 100.

Generally in a catheter, as the radius of curvature of a curved portion decreases, a kink or torsion is more liable to occur when torque is applied. However, with the catheter 10 of the present embodiment, since the radius R2 of curvature of the second curved portion 24 is set to a comparatively great dimension, the ability of the device to avoid a kink or torsion is raised. Therefore, torque can be applied readily from the proximal end side to the catheter distal end, that is, to the extreme distal end portion 30, and the direction of the catheter distal end can be changed readily. Further, when the direction of the catheter distal end is to be changed, since the displacement of the substantially linear portion 26 caused by the change of the catheter distal end is absorbed by elastic deformation of the second curved portion 24 to maintain the backup force, the catheter distal end is less likely to be disengaged from the left coronary artery opening 64.

Figure 6:
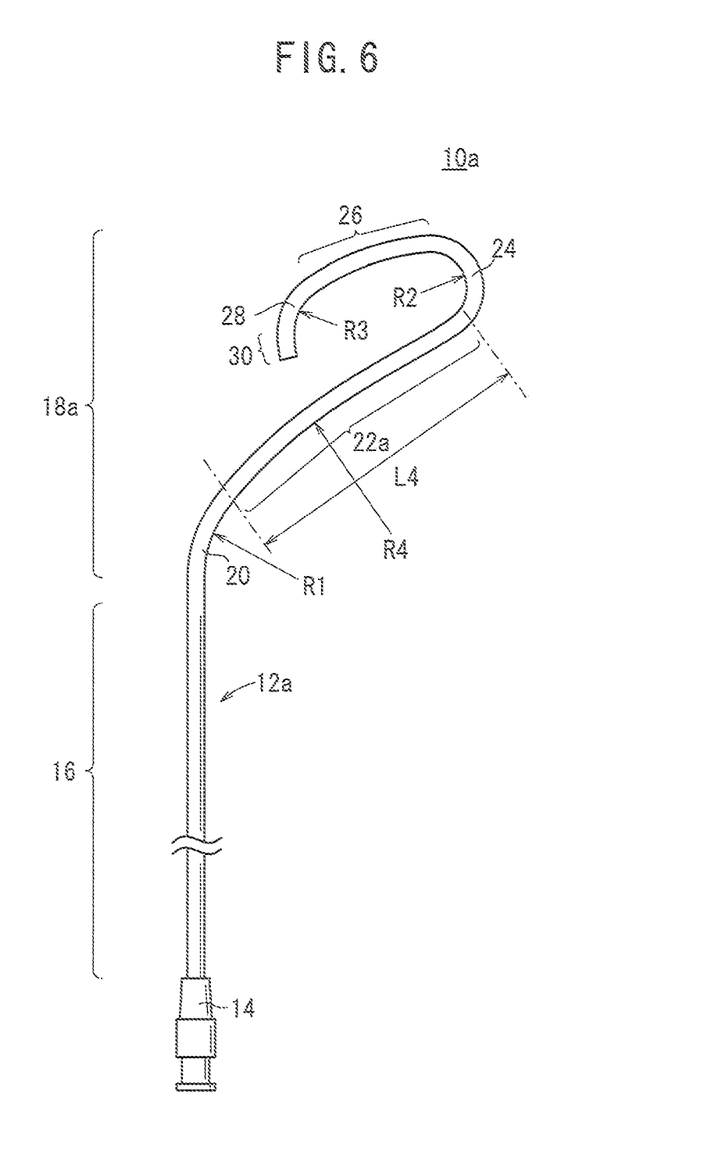
FIG. 6 is a top partial plan view showing an example of a catheter for the left coronary artery according to another embodiment of the disclosed subject matter.

FIG. 6 is a partial plan view showing a catheter 10a for the left coronary artery according to another embodiment of the disclosed subject matter. It is to be noted that, in the catheter 10a, those elements having like functions or effects to those in the catheter 10 according to the embodiment described hereinabove are denoted by like reference characters and overlapping description of them is omitted herein to avoid redundancy.

Referring to FIG. 6, the catheter 10a can include a catheter main body 12a having a hollow structure having flexibility, and a hub 14 formed at a proximal end portion of the catheter main body 12a. The outer diameter of the catheter main body 12a can be set to 2.7 mm or less, and possibly to 2.1 mm or less, over an overall length thereof similar to the catheter main body 12 described hereinabove with reference to FIG. 1.

The catheter main body 12a can have a lumen at a substantially central portion thereof and can be structured such that an inner layer, an intermediate layer and an outer layer are laminated concentrically from the inner side toward the outer side similar to the catheter main body 12 described hereinabove with reference to FIG. 2. A metal mesh can be embedded in the intermediate layer.

The catheter main body 12a can have a main body portion 16 having a substantially linear shape in a natural state thereof, and a curved portion 18a extending from the main body portion 16 to form a portion to the distal end and having a curved shape in a natural state thereof. The curved portion 18a is different from the curved portion 18 in the embodiment of FIG. 1 in that the shape of an inclined portion 22a thereof differs. In particular, the inclined portion 22a has a shape curved moderately in the same direction as that of the first curved portion 20 in a natural state. The radius (curve radius) R4 of curvature of the inclined portion 22a can be greater than the radii R1 to R3 of curvature of the first to third curved portions 20, 24 and 28 and can be set to approximately 40 to 200 mm in a natural state.

Further, although the length L4 of the inclined portion 22 is not particularly limited, it can be set to approximately 30 to 80 mm.

In the catheter 10a configured in the manner as described above, the extreme distal end portion 30 can be engaged with the left coronary artery opening 64 by a method similar to that in the case of the catheter 10 according to the embodiment of FIG. 1. In particular, the catheter 10a can be configured such that during use when the second curved portion 24 is positioned on a wall of the aorta, the extreme distal end portion 30 is moved to the neighborhood of the left coronary artery opening 64, the curved portion 18a can be rotated around a center of rotation provided by the second curved portion 24 positioned on the wall of the aorta, and the extreme distal end portion 30 is engaged with the left coronary artery opening 64.

Figure 7:
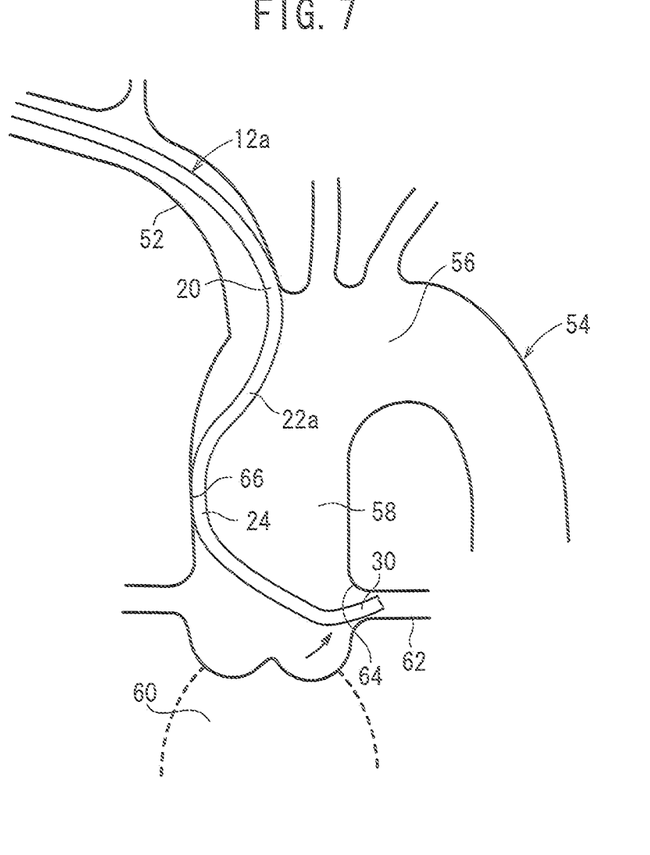
FIG. 7 is a schematic view showing the catheter for the left coronary artery of FIG. 6 in a state in which the distal end of the same is engaged with the opening of the left coronary artery.

Further, in the catheter 10a configured in the manner as described above, if the extreme distal end portion 30 which is the catheter distal end is engaged with the left coronary artery opening 64 and the second curved portion 24 is contacted with the aorta ascendens right wall 66 to establish a backup support state as seen in FIG. 7, then the second curved portion 24 can be pressed against the aorta ascendens right wall 66 by force of the inclined portion 22a which tends to restore the curved shape of the inclined portion 22a. Therefore, the stability of the backup support can be improved. Accordingly, with the embodiment of FIG. 6, the catheter 10a can have different operability and/or further improved operability.

It is to be noted that the components of the embodiment of FIG. 6 common to those of the embodiment of FIG. 1 can naturally achieve the same or similar action and effects to those achieved by the common components of the embodiment of FIG. 1. In addition, the different components can be interchanged between embodiments depending on the particular application for the device.

Various alternative materials and structures can be used without departing from the spirit and scope of the disclosed subject matter. For example, the method can include a clockwise or counterclockwise turning of the catheter.

While exemplary embodiments of the disclosed subject matter have been described using specific terms, such description is for illustrative purpose only, and it is to be understood that changes and variations may be made without departing from the spirit or scope of the following claims. All conventional art references described above are incorporated herein in their entirety by reference.

What is claimed is:

1. A catheter for a left coronary artery having a distal end configured to be introduced into an opening of the left coronary artery from an artery of an arm, comprising:
 a catheter main body including a main body portion having a substantially linear shape in a natural state thereof and a curved portion extending from the main body portion to the distal end and having a curved shape in a natural state thereof;
 the curved portion including a first curved portion, an inclined portion extending in an inclined direction with respect to the main body portion from the first curved portion, a second curved portion continuing from the inclined portion and curved in an opposite direction to a direction of curvature of the first curved portion, a substantially linear portion continuing from the second curved portion and extending to a third curved portion, and an extreme distal end portion having a substantially linear shape continuing from the third curved portion, the third curved portion being curved in a same direction as that of the second curved portion,
 wherein the curved portion includes no more than 2 undivided substantially linear sections that are (i) both located after the first curved portion and located before the extreme distal end portion and (ii) separated from one another by a single curved section;
 the catheter for a left coronary artery being shaped such that, during use, when the first curved portion is positioned in a brachiocephalic artery and the extreme distal end portion is positioned in the opening of the left coronary artery, the second curved portion contacts with an inner wall of an aorta ascendens on a side opposite to a side that includes the opening of the left coronary artery.

2. The catheter for a left coronary artery according to claim 1, wherein the substantially linear portion extends in a warped direction with respect to the inclined portion, and the substantially linear portion and the inclined portion are connected to each other by the second curved portion.

3. The catheter for a left coronary artery according to claim 1, wherein the curved portion is shaped such that, during use, when the extreme distal end portion is positioned in the opening of the left coronary artery, the extreme distal end portion is inclined with respect to an axial direction of the opening of the left coronary artery.

4. The catheter for a left coronary artery according to claim 1, wherein the curved portion exists in one single plane.

5. The catheter for a left coronary artery according to claim 1, wherein the inclined portion is curved in a same direction as the direction of curvature of the first curved portion.

6. The catheter for a left coronary artery according to claim 1, wherein the curved portion has a longitudinal axis that runs along an entire length of the curved portion, and the entire longitudinal axis exists within and intersects a single plane.

7. The catheter for a left coronary artery according to claim 1, wherein the substantially linear portion bends along a length thereof such that the substantially linear portion forms a concave surface facing towards the inclined portion.

8. The catheter for a left coronary artery according to claim 1, wherein the catheter consists of the main body portion having a substantially linear shape in a natural state thereof and the curved portion extending from the main body portion to the distal end and having a curved shape in a natural state thereof, and the curved portion consists of the first curved portion extending from the main body portion and having a first portion radius of curvature,
 the inclined portion connected to and extending from the first curved portion and having an inclined portion radius of curvature that is greater than the first portion radius of curvature,
 the second curved portion connected to and extending from the inclined portion and having a second portion radius of curvature that is less than the inclined portion radius of curvature, the substantially linear portion connected to and extending from the second curved portion, the third curved portion connected to and extending from the substantially linear portion and having a third portion radius of curvature, and the extreme distal end portion having a substantially linear shape connected to and extending from the third curved portion.

9. The catheter for a left coronary artery according to claim 8, wherein the inclined portion radius of curvature is infinitely large such that inclined portion is formed in a straight line.

10. The catheter for a left coronary artery according to claim 8, wherein the substantially linear portion is bent along its entire length such that the substantially linear portion forms a concave surface facing the inclined portion.

11. A catheter for a left coronary artery having a distal end configured to be engaged with an opening of the left coronary artery, the distal end also configured to be introduced into the opening of the left coronary artery from an artery of an arm, the catheter for a left coronary artery comprising:

a catheter main body including a main body portion having a substantially linear shape in a natural state thereof and a curved portion extending from the main body portion to the distal end and having a curved shape in a natural state thereof, the curved portion including an inclined portion extending from the main body portion in an inclined direction with respect to the main body portion via a first curved portion, a substantially linear portion continuing from the inclined portion via a second curved portion curved in a direction opposite to a direction of curvature of the first curved portion, and an extreme distal end portion having a substantially linear shape continuing from the substantially linear portion via a third curved portion curved in a same direction as a direction of curvature of the second curved portion, wherein the curved portion includes no more than 2 curved sections that are (i) both located after the inclined portion and located before the extreme distal end portion and (ii) separated from one another by an undivided substantially linear section, the catheter for a left coronary artery being shaped such that, during use, when the first curved portion is positioned in a brachiocephalic artery and the extreme distal end portion is positioned in the opening of the left coronary artery, the second curved portion contacts with an inner wall of an aorta ascendens on a side opposite to a side that includes the opening of the left coronary artery, the catheter for the left coronary artery configured such that, during use, when the second curved portion is positioned on a wall of the aorta, and the extreme distal end portion is located adjacent the opening of the left coronary artery, the curved portion is rotatable around a center of rotation defined by the second curved portion positioned on the wall of the aorta such that the extreme distal end portion is engagable with the opening of the left coronary artery.

12. The catheter for a left coronary artery according to claim 11, wherein the substantially linear portion extends in a warped direction with respect to the inclined portion, and the substantially linear portion and the inclined portion are connected to each other by the second curved portion.

13. The catheter for a left coronary artery according to claim 11, wherein the curved portion is shaped such that, during use, when the extreme distal end portion is positioned in the opening of the left coronary artery, the extreme distal end portion is inclined with respect to an axial direction of the opening of the left coronary artery.

14. The catheter for a left coronary artery according to claim 11, wherein an entire length of a longitudinal axis that extends along an entire length of the catheter exists in a single plane.

15. The catheter for a left coronary artery according to claim 11, wherein the inclined portion is curved in a same direction as the direction of curvature of the first curved portion.

16. The catheter for a left coronary artery according to claim 11, wherein the catheter consists of the main body portion having a substantially linear shape in a natural state thereof and the curved portion extending from the main body portion to the distal end and having a curved shape in a natural state thereof, and the curved portion consists of the first curved portion extending from the main body portion and having a first portion radius of curvature, the inclined portion connected to and extending from the first curved portion and having an inclined portion radius of curvature that is greater than the first portion radius of curvature, the second curved portion connected to and extending from the inclined portion and having a second portion radius of curvature that is less than the inclined portion radius of curvature, the substantially linear portion connected to and extending from the second curved portion, the third curved portion connected to and extending from the substantially linear portion and having a third portion radius of curvature, and the extreme distal end portion having a substantially linear shape connected to and extending from the third curved portion.

17. The catheter for a left coronary artery according to claim 16, wherein the inclined portion radius of curvature is infinitely large such that the inclined portion is linear.

18. An engagement method for engaging a distal end of a catheter for a left coronary artery with an opening of the left coronary artery, the catheter for the left coronary artery being configured to be introduced into the opening of the left coronary artery from an artery of an arm via the distal end of the catheter, the catheter for a left coronary artery including a catheter main body including a main body portion having a substantially linear shape in a natural state thereof and a curved portion extending from the main body portion to the distal end and having a curved shape in a natural state thereof, the curved portion including an inclined portion extending from the main body portion in an inclined direction with respect to the main body portion via a first curved portion, a substantially linear portion continuing from the inclined portion via a second curved portion curved in a direction opposite to a direction of curvature of the first curved portion, and an extreme distal end portion having a substantially linear shape continuing from the substantially linear portion via a third curved portion curved in a same direction of curvature as a direction of curvature of the second curved portion, wherein the curved portion includes no more than 2 undivided substantially linear sections that are (i) both located after the first curved portion and located before the extreme distal end portion and (ii) separated from one another by a single curved section, the catheter for a left coronary artery being shaped such that, during use, when the first curved portion is positioned in a brachiocephalic artery and the extreme distal end portion is positioned in the opening of the left coronary artery, the second curved portion contacts with an inner wall of an aorta ascendens on a side opposite to a side including the opening of the left coronary artery, the engaging method comprising:
- positioning the second curved portion on a wall of the aorta at a contact location;
- moving the extreme distal end portion to a location adjacent the opening of the left coronary artery;
- rotating the curved portion around a center of rotation defined by the contact location between the second curved portion and the wall of the aorta; and
- engaging the extreme distal end portion with the opening of the left coronary artery.

19. The engagement method of claim 18, further comprising: contacting the second curved portion of the catheter with a wall of the aorta along a length less than or equal to 10 mm.

20. The engagement method of claim 18, further comprising: maneuvering the catheter within the aorta such that the catheter simultaneously contacts both the opening of the left coronary artery, and the aorta at a single location along a length less than or equal to 10 mm.

* * * * *